United States Patent [19]

Stults

[11] Patent Number: 4,978,798

[45] Date of Patent: Dec. 18, 1990

[54] METHOD OF MAKING HALOBENZOPHENONES AND INTERMEDIATES THEREOF

[75] Inventor: Jeffrey S. Stults, Grand Island, N.Y.

[73] Assignee: Occidental Chemical Corporation, Niagara Falls, N.Y.

[21] Appl. No.: 434,742

[22] Filed: Nov. 13, 1989

[51] Int. Cl.$^5$ .............................................. C07C 45/65
[52] U.S. Cl. .................... 568/316; 570/144; 570/184; 568/323
[58] Field of Search ................ 568/323, 376; 570/144, 570/184

[56] References Cited

U.S. PATENT DOCUMENTS

| | | | |
|---|---|---|---|
| 3,017,440 | 1/1962 | Entemann | 570/184 |
| 4,263,458 | 4/1981 | Bowden | 568/323 |
| 4,320,224 | 3/1982 | Rose et al. | 568/323 |
| 4,453,009 | 6/1984 | Vamaguchi et al. | 568/323 |
| 4,453,012 | 6/1984 | Desbois | 568/323 |

FOREIGN PATENT DOCUMENTS

| | | | |
|---|---|---|---|
| 0092627 | 11/1983 | European Pat. Off. | 568/323 |
| 0092628 | 11/1983 | European Pat. Off. | 568/323 |
| 58-131924 | 8/1983 | Japan | 570/184 |
| 59-139329 | 8/1984 | Japan | 570/144 |
| 2200632 | 1/1988 | United Kingdom . | |

OTHER PUBLICATIONS

Feiser et al., "Reagents for Organic Synthesis", p. 1026, (1967).

*Primary Examiner*—James H. Reamer
*Attorney, Agent, or Firm*—James F. Tao; Richard D. Fuerle

[57] ABSTRACT

Disclosed is a method of making a bisphenyl dihalomethane by reacting a trihalomethylbenzene with a halobenzene and a Lewis acid. The bisphenyl dihalomethane can than be reacted with water to form a halobenzophenone. In an optical third step ring chlorines that are present can be replaced with fluorines and, in a final step, any remaining chlorines can be removed to leave a fluorobenzophenone. The process is particularly useful in making 4,4'-difluorobenzophenone, which is in turn useful in making polyetheretherketones.

22 Claims, No Drawings

METHOD OF MAKING HALOBENZOPHENONES AND INTERMEDIATES THEREOF

BACKGROUND OF THE INVENTION

This invention relates to a process for preparing halobenzophenones and intermediates made in their preparation. In particular, it relates to a process for preparing 4,4'-difluorobenzophenone.

The compound 4,4'-difluorobenzophenone is useful in making high molecular weight polyetheretherketones (PEEK). See, for example, U.S. Pat. No. 3,320,224, herein incorporated by reference. At the present time, 4,4'-difluorobenzophenone is made commercially by a process described in U.S. Pat. No. 4,263,458. In that process, methylene dianiline is reacted with hydrogen fluoride to produce the fluoride salt. This fluoride salt is explosive and handling large quantities of it can present a considerable safety hazard. In the next step, the fluoride salt is thermally decomposed and oxidized to form 4,4'-difluorobenzophenone. Because of the explosive nature of the fluoride salt a less dangerous chemical route to produce the product would be desirable.

SUMMARY OF THE INVENTION

I have discovered that 4,4'-difluorobenzophenone can be produced from 3,4-dichlorobenzotrifluoride and 1,2-dichlorobenzene by a process involving four steps. The four step process is rather unusual because it begins with dichlorobenzene, even though one of the chlorines is later removed, rather than with monochlorobenzene, which is less expensive and which does not require the extra step of removing a chlorine. While it may sound illogical to pay more for a compound having an extra chlorine and then remove the extra chlorine, in this way I am able to avoid the production of mixtures of compounds that are difficult to separate. Also, the use of dichlorobenzene enhances the rate of the fluorination reaction because it is easier to replace chlorines with fluorines when a chlorine is present which is ortho to another chlorine. Unlike the prior process for producing 4,4'-difluorobenzophenone, the process of this invention does not require the production of any intermediate which is explosive or unusually hazardous. In addition to producing 4,4'-difluorobenzophenone, the process of this invention is also useful in producing related halobenzophenones. The intermediate compounds produced by each of the steps are also useful in various chemical processes.

DESCRIPTION OF INVENTION

In this invention halobenzophenones are produced by a process that involves four steps. The first step involves a reaction of a trihalomethylbenzene with a halobenzene and a Lewis acid. The trihalomethylbenzene is a compound having the general formula

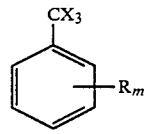

In the above general formula "R" can be hydrogen, halogen, or alkyl of any length. The R group is preferably halogen as those compounds are more useful; chlorine and fluorine are particularly preferred. In the above general formula "m" indicates the number of R groups and can be 1 to 5, but is preferably 1 to 4, and is most preferably 2, where the two R groups are in the 3,4 position, as those compounds have the greatest utility.

The halobenzene is a compound having the general formula

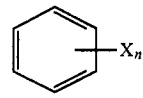

In the above general formula "X" is halogen and is preferably chlorine or fluorine (most preferably chlorine) as those halobenzenes yield more valuable products. In the formula, "n" can be 2 to 5, but cannot be 6 as that compound will not react well, and cannot be 1 as that compound produces mixtures which require difficult separation procedures. It is preferable that the halogens be arranged on the benzene ring so that the halobenzene is symmetrical, as this avoids the formation of mixtures of different isomers. A halobenzene is symmetrical if it has a plane of symmetry or an axis of symmetry.

The Lewis acid has the general formula $MX_p$ where "X" is halogen, preferably chlorine or fluorine, and "p" is the valence of M. Examples of suitable Lewis acids include $AlCl_3$, $BF_3$, $SbCl_3$, $SbCl_5$, $SbF_3$, $SbF_5$, and $MoCl_qF_{6-q}$ where "q" equals 0 to 6. The preferred Lewis acid is aluminum trichloride because that compound is inexpensive and works well.

In the first step reaction the trihalomethylbenzene and the halobenzene react stoichiometrically. However, it is preferable to have excess halobenzene present to serve as a solvent for the trihalomethylbenzene as this increases the reactivity and obviates the necessity for a separate solvent. A catalytic amount of the Lewis acid should be present and, while less than one equivalent can be used, it is preferable to use about 1 to about 2 equivalents to speed the reaction. The temperature of the reaction is not critical and the reaction will proceed at a temperature of about 0° to about 80° C. At lower temperatures, however, the reaction is impractically slow and at temperatures over 80° C. byproducts may be formed.

The product of the first reaction is a bisphenyl dihalomethane having the general formula

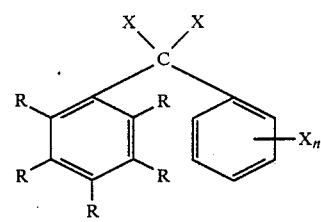

where "R," "X," and "n" were previously defined.

In the second step of the process of this invention the bisphenyl dihalomethane formed in the first step is reacted with water to form a halobenzophenone having the general formula

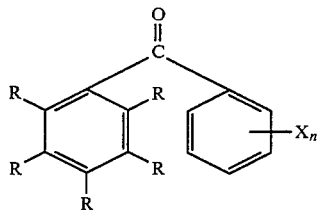

At least one equivalent of water is needed for this reaction, and the reactants are preferably refluxed to speed the reaction. It is also preferable to include about 20 to about 50% of a recrystallization solvent. The purpose of the recrystallization solvent is to cause the precipitation of the halobenzophenone upon cooling of the reaction mixture. Suitable recrystallization solvents are well known in the art and include ethanol, toluene, and chlorobenzene. A mixture of about 90 to 95 percent by weight ethanol and about 5 to about 10 percent water is preferred.

The purpose of the third step in the process of this invention is to replace some, but not all, of any chlorines that may be present on the benzene rings of the halobenzophenone. If no chlorines are present on the halobenzophenone, the third step in the process can be skipped. If only a single chlorine is present, the third step is optional. To illustrate the third step in the process of this invention, if the trihalomethylbenzene is 3,4-dichlorobenzotrifluoride, the halobenzene is 1,2-dichlorobenzene, and the Lewis acid is aluminum trifluoride, they react to form bis-(3,4-dichlorophenyl)dichloromethane which is reacted with water to form 3,3',4,4'-tetrachlorobenzophenone:

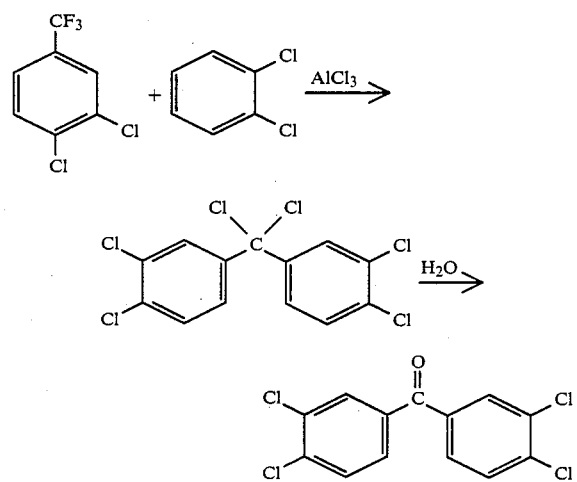

In the third step the 3,3',4,4'-tetrachlorobenzophenone is reacted with a fluorinating agent to produce about 99 percent 3,3'-dichloro-4,4'-difluorobenzophenone and about 1 percent 3,3',4-trichloro-4'-fluorobenzophenone.

The result of the third step is that some, but not all, of the chlorines are replaced with fluorines. Any fluorinating agent can be used in this reaction, but the preferred fluorinating agents are potassium fluoride and cesium fluoride as they are most effective. The reaction is preferably conducted in a polar aprotic solvent such as methylsulfone, sulfolane, or dimethylsulfoxide; methylsulfone is preferred as it minimizes formation of any byproducts. The third reaction is performed at a temperature in excess of 200° C. and preferably at a temperature between 230° and 250° C. If a mixture of products is produced, they can be separated by recrystallization or distillation or other suitable process.

In the fourth step of the process of this invention, any chlorines remaining on the benzene ring can be removed using a dechlorinating agent. For example, 3,3'-dichloro-4,4'-difluorobenzophenone is dechlorinated to produce 4,4'-difluorobenzophenone:

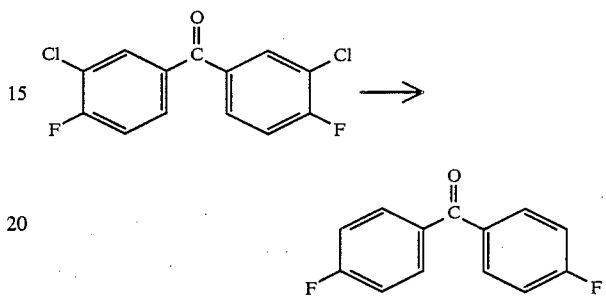

Suitable dechlorinating agents include, for example, palladium on carbon (e.g. 10 wt % palladium on 90 wt % carbon) with sodium formate, or with a mixture of formic acid and triethylamine. The fourth reaction is preferably performed in a solvent such as ethanol or methanol at a temperature of about room temperature to reflux.

The final product, a halobenzophenone, can be used in a variety of chemical processes, but is particularly useful in making polyetheretherketones (PEEKs). The PEEKs are used for electrical coatings, airplane struts, decorative finishes, hydraulic lines, microwave oven parts, and other applications where high strength and high temperature stability are needed.

The following examples further illustrate this invention.

EXAMPLE 1

Preparation of 3,3',4,4'-Tetrachlorobenzophenone.

Aluminum chloride (16 g.) was slurried with 1,2-dichlorbenzene (40 ml.). A solution of 3,4-dichlorobenzotrifluoride (21.5 g.) in 1,2-dichlorobenzene (40 ml.) was added to the aluminum chloride slurry over 1.25 hours. The solution became dark red and viscous. The reaction mixture was stirred for 88 hours at room temperature and then heated to 70° C. for 6 hours. The reaction contents were poured into water and the aqueous portion was extracted with methylene chloride. The combined organic extracts were dried over magnesium sulfate and filtered. The solvents were removed on a rotary evaporator (methylene chloride) followed by a bulb-to-bulb distillation to remove most of the dichlorobenzene (85° C., 10 torr). Aqueous ethanol (U.S. Industrial Chemical Company, special denatured ethanol, 10% water added, 100 ml. total) was added to the reaction product and the contents of the flask were refluxed overnight. The solution was allowed to cool and the solid was collected and washed with ethanol to give a whitish solid (25.7 g., 80% yield). An analytical sample was obtained by recrystallization from ethanol/toluene (3.5–1) mp = 144.

EXAMPLE 2

Preparation of 3,3'-Dichloro-4,4'-difluorobenzophenone.

Potassium fluoride (51.1 g., 0.91 mole, used as received from Aldrich), methyl sulfone (199 g), and 3,3'4,4'-tetrachlorobenzophenone (104 g) were heated to 230° C. (bath temperature) for approximately 47 hours. The reaction was poured into water (2 L.). The aqueous phase was extracted with ether (250 ml) followed by methylene chloride (500 ml.). The ether phase was washed with water to remove methyl sulfone, then was dried over magnesium sulfate. The ether was removed on a rotary evaporator and the resulting solid was purified via a bulb-to-bulb distillation, first at 100° C. to remove methyl sulfone, then at 145°–155° C. air temperature (0.3 mm) to give 3,3'-dichloro-4,4'-difluorobenzophenone (19.5 g) as a white solid. Total yield was 60.2 g (65%). An analytical sample of 3,3'-dichloro-4,4'-difluorobenzophenone was obtained by recrystallization from methanol, mp=93° C.

EXAMPLE 3

Preparation of 4,4'-Difluorobenzophenone.

3,3-Dichloro-4,4'-difluorobenzophenone (1 g.), sodium formate (0.92 g.), ethanol (6 ml.) and 10% palladium on carbon were added together at room temperature and the reaction stirred for 27 hours. The reaction mixture was diluted with methylene chloride and filtered through magnesium sulfate. The organic phase was decanted after some solid precipitated upon standing. The solvents were removed on a rotary evaporator. The resulting solid was purified via a bulb-to-bulb distillation (150° C. air temperature/2 mm.) to give 4,4,-difluorobenzophenone as a white solid (0.55 g, mp=103°–104° C.) in 73% yield.

I claim:

1. A method of making a fluorinated benzophenone comprising
    (1) reacting a trihalomethyl benzene having the general formula

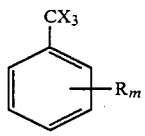

with a halobenzene having the general formula

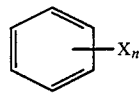

and a Lewis acid having the general formula $MX_p$, to form a bisphenyl dihalomethane, where each R is independently selected from hydrogen, alkyl, or X, each X is independently selected from halogen, M is aluminum, boron, antimony, or molybdenum, "m" is 1 to 5, "n" is 2 to 5, "p" is the valence of M, and at least two of X's in said halobenzene are chlorine;
    (2) reacting said bisphenyl dihalomethane with water to form a halobenzophenone having the general formula

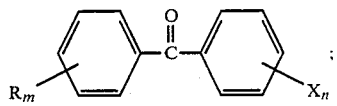

(3) reacting said halobenzophenone with a fluorinating agent whereby at least one chlorine, but not all chlorines, is replaced with a flurorine; and
    (4) removing all remaining chlorines.

2. A method according to claim 1 wherein R is halogen.

3. A method according to claim 2 wherein R is chlorine or fluorine.

4. A method according to claim 3 wherein "m" is 1 to 4.

5. A method according to claim 4 wherein "m" is 2.

6. A method according to claim 5 wherein the 2 R groups are in the 3,4 position.

7. A method according to claim 1 wherein each X on said halobenzene is independently selected from chlorine and fluorine.

8. A method according to claim 7 wherein each X on said halobenzene is chlorine.

9. A method according to claim 1 wherein said halobenzene is symmetrical.

10. A method according to claim 1 wherein said Lewis acid is $AlCl_3$.

11. A method according to claim 1 wherein sufficient liquid halobenzene is present to solubilize said trifluoromethyl benzene.

12. A method according to claim 1 wherein 1 to 2 equivalents of said Lewis acid are present.

13. A method according to claim 1 wherein said reaction with water is performed in the presence of a recrystallization solvent.

14. A method according to claim 13 wherein said recrystallization solvent is ethanol.

15. A method according to claim 1 wherein said fluorinating agent is KF or CsF.

16. A method according to claim 1 wherein said reaction with said fluorinating agent is performed in a polar aprotic solvent at a temperature over 200° C.

17. A method according to claim 1 wherein at least two of said R or X are chlorines that are ortho to each other.

18. A method of making 4,4'-difluorobenzophenone comprising
    (1) reacting 3,4-dichlorobenzotrifluoride with 1,2-dichlorobenzene and $AlCl_3$ to form bis(3,4-dichlorophenyl) dichloromethane;
    (2) reacting said bis(3,4-dichlorophenyl) dichloromethane with water to form 3,3',4,4'-tetrachlorobenzophenone;
    (3) reacting said 3,3'4,4'-tetrachlorobenzophenone with a fluorinating agent to make 3,3'-dichloro-4,4'-difluorobenzophenone; and
    (4) reacting said 3,3'-dichloro-4,4'-difluorobenzophenone with a dechlorinating catalyst to produce said 4,4'-difluorobenzophenone.

19. A method according to claim 18 wherein said fluorinating agent is KF or CsF.

20. A method of making a fluorinated benzophenone comprising
    (1) reacting a trihalomethyl benzene having the general formula

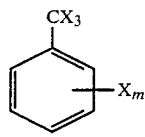

with a halobenzene having the general formula

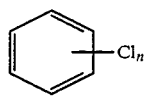

and a Lewis acid having the general formula MXp to form a bisphenol dihalomethane, where each X is independently selected from chlorine and fluorine, "m" is 1 to 4, "n" is 2 to 5, and "p" is the valence of M;

(2) reacting said bisphenol dihalomethane with water to form a halobenzophenone;

(3) reacting said halobenzophenone with a fluorinating agent whereby at least one of said chlorines derived from said halobenzene, but not all of said chlorines, is replaced with a fluorine; and (4) removing all remaining chlorines.

21. A method according to claim 20 wherein said fluorinating agent is KF or CsF.

22. A method according to claim 20 wherein said trihalomethyl benzene is a trifluoromethyl benzene and $X_m$ is $Cl_m$.

* * * * *